United States Patent [19]

Hale

[11] Patent Number: 5,030,334
[45] Date of Patent: Jul. 9, 1991

[54] OZONE MEASURING METHOD
[75] Inventor: John M. Hale, Meinier, Switzerland
[73] Assignee: Orbisphere Laboratories, Inc., Switzerland
[21] Appl. No.: 504,663
[22] Filed: Apr. 3, 1990

Related U.S. Application Data

[63] Continuation of Ser. No. 329,679, Mar. 28, 1989, Pat. No. 4,956,063.

[30] Foreign Application Priority Data

Mar. 31, 1988 [EP] European Pat. Off. ........ 88810217.5

[51] Int. Cl.$^5$ ............................................. G01N 27/26
[52] U.S. Cl. ........................... 204/153.17; 204/153.1; 204/401
[58] Field of Search ................. 204/153.1, 401, 153.17

[56] References Cited

U.S. PATENT DOCUMENTS

| 2,913,386 | 11/1959 | Clark | 204/415 |
| 4,176,032 | 11/1979 | Stevenson | 204/415 |
| 4,711,245 | 12/1987 | Higgins et al. | 128/635 |

FOREIGN PATENT DOCUMENTS

| 52-497 | 5/1978 | Japan . |
| 150196 | 11/1979 | Japan . |
| 22150 | 2/1980 | Japan . |
| 54344 | 5/1981 | Japan . |
| 56-748 | 4/1982 | Japan . |
| 3898 | 1/1987 | Japan . |

OTHER PUBLICATIONS

John H. Stanley et al., Anal. Chem., vol. 51, No. 13, pp. 2144–2147, Nov. 1979.

Josef Vesely et al., "Analysis with Ion—Selective Electrodes", pp. 96–104, (1978).

*Primary Examiner*—John F. Niebling
*Assistant Examiner*—Arun S. Phasge
*Attorney, Agent, or Firm*—Wigman & Cohen

[57] ABSTRACT

Quantitative determination of ozone contained in a fluid by an amperometric method comprises the steps of:
(A) providing an amperometric cell having a sensing electrode, a counter electrode, an aqueous electrolyte in contact with the sensing electrode and the counter electrode, and a membrane that is substantially impermeable to the electrolyte but permeable to gaseous media including ozone and oxygen for containing the electrolyte within the cell and for separating it from the fluid maintained external to the cell;
(B) providing in the aqueous electrolyte a redox catalyst for chemically transforming the ozone upon its permeation through the membrane into an intermediary electroactive species capable of generating upon reaction with the sensing electrode an indicative electric signal in proportion with a concentration of the ozone in the fluid;
(C) applying a predetermined potential across the sensing electrode and the counter electrode;
(D) measuring a cell current generated by reaction of the intermediary electroactive species with the sensing electrode; and
(E) deriving from the cell current a signal that is indicative of the concentration of the ozone in the fluid.

Further, a calibration method for use in determination of ozone and other highly reactive chemical agents is disclosed.

11 Claims, 2 Drawing Sheets

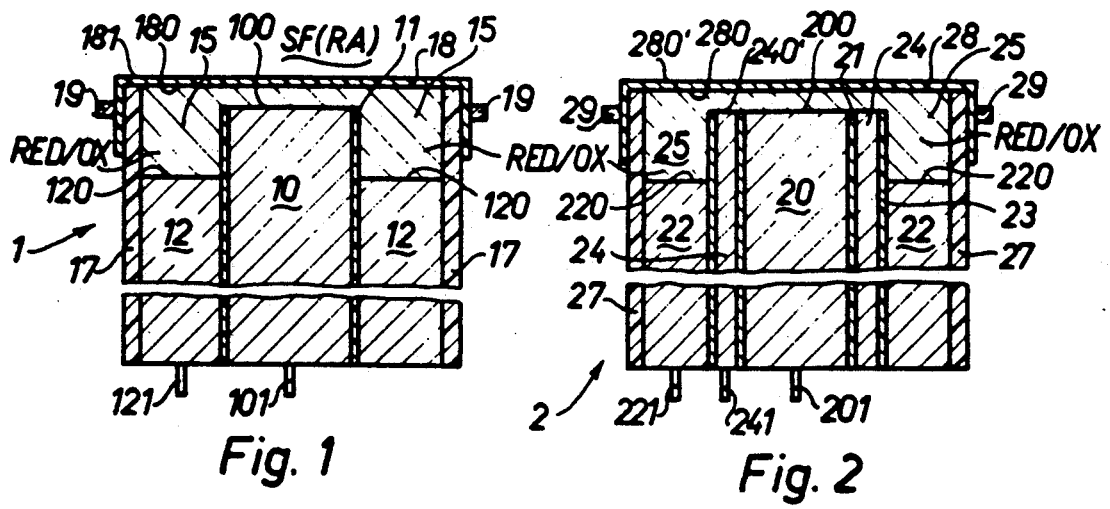
Fig. 1
Fig. 2
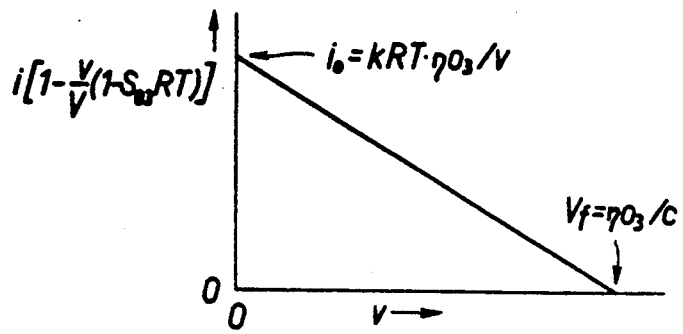
Fig. 3A
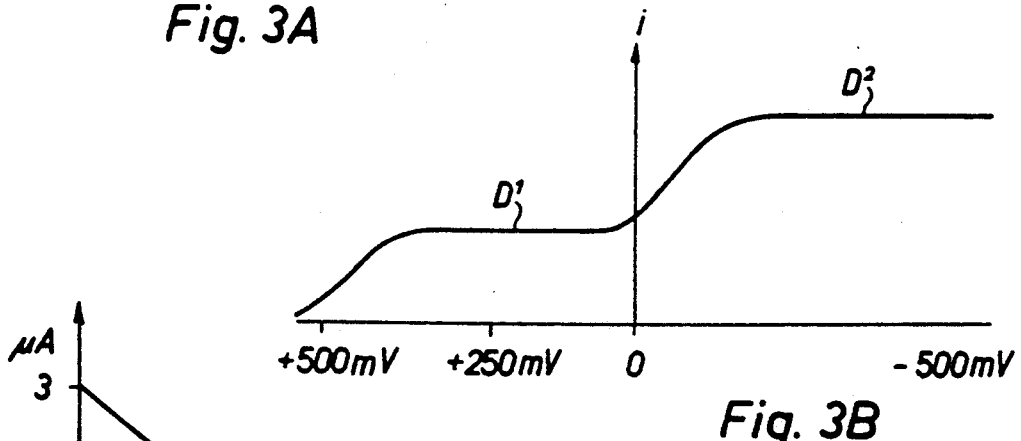
Fig. 3B
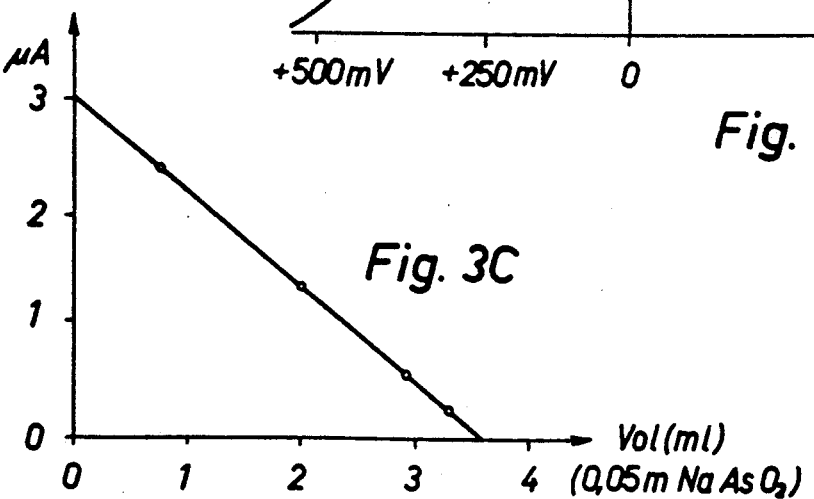
Fig. 3C

OZONE MEASURING METHOD

This is a continuation of co-pending application Ser. No. 07/329,679 filed on Mar. 28, 1989 now U.S. Pat. No. 4,956,063.

BACKGROUND OF THE INVENTION (1) Field of the Invention

This invention generally relates to amperometry, i.e. the apparative and operative means for quantitative electroanalytical determination of the concentration of an electroactive species of interest in a given sample and specifically to an amperometric cell of the type known as Clark cell and disclosed, e.g. in U.S. Pat. No. 2,913,386, as well as to amperometric methods using such cells. The term "electroactive species" as used herein generally refers to a substance, or substance component, that is capable of being oxidized or reduced by a suitably charged electrode.

While many modifications of the Clark cells are known, they share the following apparatus features:
(1) a sensing electrode which may be cathodic or anodic;
(2) a corresponding counter electrode;
(3) an aqueous electrolyte in contact with both the sensing electrode and the counter electrode; and
(4) a membrane that separates the aqueous electrolyte from the sample (termed to be "external" to the cell) and is essentially impermeable to the aqueous electrolyte yet permeable to the electroactive species of interest (also termed EASI).

Amperometric cells having the above features (1) to (4) are also termed MEACs (Membrane-Enclosed Amperometric Cells) herein. The sample external to the MEAC and containing the electroactive species generally is a fluid and may be a gas or a liquid in contact with the side or surface of the membrane opposite to that contacted by the electrolyte.

The common operative means of electroanalysis with MEACs include the steps of:
providing an amperometric cell having a sensing electrode, a counter electrode, an aqueous electrolyte in contact with the sensing electrode and the counter electrode, and a membrane that is substantially impermeable to the electrolyte but permeable to the EASI for containing the electrolyte within the cell and for separating it from the fluid maintained external to the cell;
applying a predetermined potential across the sensing electrode and the counter electrode;
measuring a cell current generated by reaction of an electroactive species with the sensing electrode; and
deriving a signal from such current that is indicative of the concentration of the EASI in the fluid sample.

(2) Description of the Prior Art

While there is no theoretical limit to the applicability of these amperometric means to the determination of concentrations of any particular electroactive species, considerable practical difficulties have been encountered when attempting to use commercial MEACs for uses other than oxygen measurements. For example, the above mentioned U.S. Patent to Clark, in addition to disclosing an oxygen monitoring method that is eminently suitable for practical purposes, sets forth that various other and either electro-reducible or electro-oxidizable species can be measured. However, practical implementation of amperometric determination of hydrogen concentration, for example, proved to be very difficult, c.f. U.S. Pat. No. 4,563,249, while measuring strongly oxidizing substances, such as ozone, seemed to call for a radical deviation from accepted MEAC structures, e.g. using rotating electrodes as suggested in U.S. Pat. No. 3,960,673, or to require non-steady state operating conditions, or to use completely different systems, such as disclosed in U.S. Pat. No. 4,409,183. The performance of commercially available amperometric cells for measuring ozone concentrations leaves much to be desired as will be explained in more detail below, notably with regard to very long stabilization periods that would not be acceptable for routine monitoring purposes of the type required in modern manufacturing or processing plants.

As a matter of practice ozone ($O_3$) can be regarded as a "strong" oxidizing agent which, when measured on a normal hydrogen electrode scale at pH=0° and 25° C., generally exhibits a potential of at least about +1.3 Volts and which tends to show "slow stabilization" and "poor reproducibility" when analyzed by conventional methods with MEACs.

"Slow stabilization" means that an unduly long period of time is required for the response of a MEAC to a step change of the concentration of the electroactive species of interest (also referred to herein as EASI), e.g. upon sudden elimination of the EASI from the fluid that is external to the MEAC. While such response is asymptotic as a matter of principle, as a matter of practice a "reasonable" approximation to stability is expected to occur with a commercial MEAC within a couple of minutes, say typically in less than 10 minutes and preferably within 5 minutes, in a system suitable for routine measurements.

However, when using a commercially available MEAC for ozone detection, stabilization may require periods of up to 3 hours and this, obviously, is not suitable for quantitative measurement intended for routine operation in manufacturing or processing plants.

As regards an "acceptable degree" of reproducibility of measurement, this again is a matter of practice rather than theory; in commercial amperometry, however, one would normally expect a degree of reproducibility of "at least" 10% meaning a maximum deviation of repeated measurements under identical conditions of not more than 10% and typically better than 5%, i.e. ±5% deviation and preferably ±1% deviation. So far and according to tests made in the course of research leading to the present invention, such a degree of reproducibility cannot generally be achieved in routine operations with commercially available ozone measuring devices regardless of their working principle; this is evidenced by the fact that there is an acute need for commercial ozone measurement means which would satisfy these requirements.

In sum, amperometric routine measurements with commerically available MEACs tend to have one or both of the above defects when the EASI is ozone and it can be said with confidence that conventional electroanalytical methods are not generally suitable for effective and efficient quantitative determination of ozone.

Further, no simple yet reliable calibration methods are available for measurement of highly reactive substances, notably when the latter are such as typically ozone.

OBJECTS AND BRIEF SUMMARY OF THE INVENTION

Hence, it is a main object of the present invention to provide for an improved MEAC that permits measuring the concentration of ozone with both an acceptable period of stabilization as well as a satisfactory degree of reproducibility as defined above.

A further essential object of the invention is an amperometric method capable of permitting improved stability and reproducibility when determining the concentration of ozone.

Another important object is an improved method of calibrating probes and other devices for quantitative determination of ozone and other substances that are highly reactive.

Further objects will become apparent as the specification proceeds.

Now, it has been found according to the present invention that these objects and further advantages will be achieved by an amperometric method for quantitative determination of ozone contained in a fluid comprising the steps of:

(A) providing an amperometric cell having a sensing electrode, a counter electrode, an aqueous electrolyte in contact with the sensing electrode and the counter electrode, and a membrane that is substantially impermeable to the electrolyte but permeable to the ozone for containing the electrolyte within the cell and for separating it from the fluid maintained external to the cell;

(B) providing in the aqueous electrolyte a redox catalyst for chemically transforming the ozone upon its permeation through the membrane into an intermediary electractive species capable of generating, upon reaction with the sensing electrode, an indicative electrical signal in proportion with the concentration of the ozone in the fluid;

(C) applying a predetermined potential across the sensing electrode and the counter electrode;

(D) measuring a cell current generated by reaction of the intermediary electroactive species with the sensing electrode; and (E) deriving from the cell current a signal that is indicative of the concentration of the ozone in the fluid.

The term "redox catalyst" as used herein is intended to refer to a chemical substance that is capable to exist in at least two different states of oxidation (implying "oxidation" in an electrochemical sense rather than necessarily implying the presence of oxygen), both of which states or forms are not normally volatile and are soluble at least to some extent (typically at least about 0.1 mole per liter of water at room temperature) in the aqueous electrolyte.

Further, the redox catalyst should not, under the specific conditions of a given electrolyte and operation of the MEAC, tend to hydrolyze. Also, the redox catalyst must be capable to react—generally in an aqueous medium and under the conditions of MEAC operation—virtually instantaneously with the ozone (the latter being also termed "reactive" agent for short) when forming the intermediate electroactive species (also termed "transfer" species for short).

The phrase "virtually instantaneous reaction of the reactive agent with the redox catalyst" is used herein to indicate such a high rate of reaction that any part or molecule of the reactive agent that has permeated from the external sample through the membrane into the electrolyte layer adjacent the membrane will react with the redox catalyst and form the intermediate electroactive or transfer species so rapidly that substantially no reactive agent proper could reach the surface of the sensing electrode even if the elelctrolyte layer between the inner surface of the membrane and the electrolyte-exposed surface of the sensing electrode is very thin, e.g. in the range of from 1 to 100 $\mu$m (micrometer). In other words, the electrode reaction that produces the indicative signal in a cell according to the invention exclusively is the "indirect" electrochemical reaction of the transfer species with the sensing electrode and not a "direct" electrochemical reaction of the reactive agent with the electrode.

Generally, when the reactive agent is ozone, the redox catalyst present in the electrolyte is the reduced (or rather a reduced) component of a redox system. For example, a preferred redox catalyst in the electrolyte is the bromide ($Br^-$) state or form of the bromide/bromate ($Br^-/BrO_3^-$) or the bromide/hypobromite/bromite ($Br^-/BrO^-$) redox system.

Further, since the cell according to the invention is to respond quickly to a step change as explained above, the rates of the electrochemical reactions involved and notably the rate of electrochemical reaction of the intermediate or transfer species (formed by chemical reaction of the reactive agent and the redox catalyst) should be "fast".

In other words, the current which forms the indicative electrical signal should be controlled by diffusion, i.e. the rate of diffusion of the reactive agent through the membrane, rather than by the electrode reaction, i.e. by the rate of the reaction of the transfer species at the sensing electrode, or expressed mathematically:

$$\text{Electrode reaction rate } k \text{ (cm} \cdot \text{s}^{-1}) >> \frac{D_m \cdot S_m}{Z_m \cdot S_e} \quad \text{(Eq. 1)}$$

in which $D_m$ is the diffusion rate of the reactive agent through the membrane, $S_m$ is the solubility of the reactive agent in the membrane, $Z_m$ is the thickness of the membrane and $S_e$ is the solubility of the reactive agent in the electrolyte.

In practice, the parameter "k" or "left value" of Eq. 1 should in any given instance be at least about 100 times greater than the membrane-and-solubility parameters or "right value" of Eq. 1.

These parameters and their impact upon MEAC amperometry are well understood in the art, c.f. Chapter 1 by Hale, J. M., in the Monography "Polarographic Oxygen Sensors", edited by Gnaiger, E. and Forstner, H., Springer 1983, so that no further discussion of this aspect is needed herein.

Further, while many specific values for calculation of Eq. 1 are available in the literature, a few simple experiments made in line with the specific examples given herein will be sufficient to verify that a sufficiently large value of "k" in Eq. 1 is maintained or what changes regarding the electrolyte including the redox catalyst or other cell parameters could be made for optimization in a given case.

Redox systems in general are well known in the analytical art and for use in chemical analysis. For example, potassium iodide is known as a reagent for the purpose of determination of ozone (cf. Environment Science and Technology, Vol. 7, No. 1, page 65) and could be used as a redox catalyst in the aqueous electrolyte of a MEAC according to the invention for ozone measurement but is less preferred than sodium or potassium bromide for the same purpose.

The use of redox catalysts or redox systems in the electrolyte of a MEAC for determination of ozone has not, to the best of Applicant's knowledge, ever been suggested and is, in fact, contrary to the conventional teachings of amperometry when applied e.g. to oxygen monitoring. The generally accepted basic requirement for such an electrolyte used to be that solute constituents should not be allowed to change their state of oxidation under the operating conditions, mainly the applied cell voltage between the electrodes. For example, sodium chloride is a typical electrolyte constituent of MEAC electrolytes and its suitability was believed to depend upon the fact that the potentials required for oxidizing it (to form chlorine, $ClO^-$, $ClO_2^-$ or $ClO_3^-$, for example) would not occur when the MEAC was normally operated, e.g. for oxygen sensing. By the same token, the bromides of potassium or sodium were not preferred because they could be transformed into $BrO^-$, $BrO_2^-$ or $BrO_3^-$ even more readily than the chlorides. The inventive teaching actually reverses this objection against using "electro-labile" or "redoxing" electrolyte components and, by this, resolves the above mentioned problems of amperometric determination of ozone.

While not wishing to be bound by a specific theory, it can be assumed that a main reason for the problems encountered in MEAC-amperometry with ozone is its tendency to react with the water constituent of the electrolyte; possibly, the delay of stabilization mentioned above might be due to the formation of products of reaction of ozone with water resulting in pH changes or in dissolved gas content. A stable and indicative current output might then not be achieved at all, or only after reaching a certain plateau or level of formation or dissociation of possibly labile yet energetically defined products of reaction of ozone and water.

Now, according to the invention, the redox catalyst of the electrolyte would function in the manner of a "reversible getter", that is, react instantly with the agent of interest to transform the latter into a less active product, i. e. oxygen from ozone, and react with the sensing electrode so as to produce an indicative current while simultaneously being reformed into its primary state. Thus, the intermediate or secondary state of the redox catalyst serves as an "intermediary" electroactive species or "transfer species".

Of course, the concentration of the redox catalyst should be sufficiently high to make sure that the probability that the permeated ozone will react chemically with the redox catalyst prior to reaching the sensing electrode approaches unity. Concentrations of the redox catalyst in the broad range of from 0.05 to 5 mole per liter will be operative in general, it being understood that the concentration of the ozone in the external sample fluid may have an impact and that the upper limit of the concentration of the redox catalyst in the electrolyte is not critical except that solubility limits may be reached. While the presence of undissolved redox catalyst may not be harmful, it does not normally provide an advantage since the very term "redox catalyst" as used herein implies that it is not "consumed" in any significant extent but that the formation of the transfer species by chemical reaction with ozone will be fully reversed by reformation of the redox catalyst as a consequence of the electrochemical reaction of the transfer species with the sensing electrode.

Some representative specific examples of redox catalyst for use in the invention are as follows:

$Tl(I)^+$, e.g. as $Tl_2SO_4$ $Fe(II)^{++}$, e.g. as $FeSO_4$ $(IrCl_6)^{-3}$, e.g. as $Na_3(IrCl_6)$ $(AsO_2)^-$, e.g. as $Na(AsO_2)$ $Br^-$, e.g. as KBr.

However, as mentioned previously, such substances are well known per se in the art and suitable selection for the present invention is well within the reach of one skilled in the art given the above explanations.

Further, the invention helps to solve a crucial problem in quantitative determination of highly reactive agents as well as chemically labile substances, such as typically ozone, caused by the lack of simple yet effective on-site calibration. For example, while an oxygen probe can be most easily calibrated with ambient air (or air-saturated water) onsite universally because of the constant oxygen concentration of normal ambient air, there are no easily available (and storable) standard samples of such reactive and labile substances as, typically, ozone; while ozone generators could be used for calibration, the ozone output of such a generator cannot be guaranteed and/or need not be constant if operating conditions on-site cannot be fully controlled.

It has now been found, according to the invention, that a reasonably exact and reproducible on-site calibration of a MEAC for use in determining reactive and labile substances can be obtained if on-site calibration is made but with a stable electroactive substance, such as ambient air oxygen, and if—in addition to standard compensation for temperature or the like environmental parameters—a correlation is made on-site between the stable-substance-calibration and a previously determined factor derived from the permeation rate of the stable substance (used for on-site calibration) and the reactive substance for a given type of membrane.

BRIEF DESCRIPTION OF THE DRAWINGS

The invention will be explained in more detail by way of example and not limitation with reference to the annexed drawings in which:

FIG. 1 is a diagrammatic cross-sectional view of a membraneenclosed amperometric cell or MEAC including an electrolyte according to the invention shown in a simplified and fragmented presentation;

FIG. 2 is a view similar to that of FIG. 1 but with an optional guard electrode;

FIG. 3A, 3B and 3C are graphs to illustrate certain functions involving a current;

DETAILED DISCUSSION OF THE PREFERRED EMBODIMENTS

Figure 4:
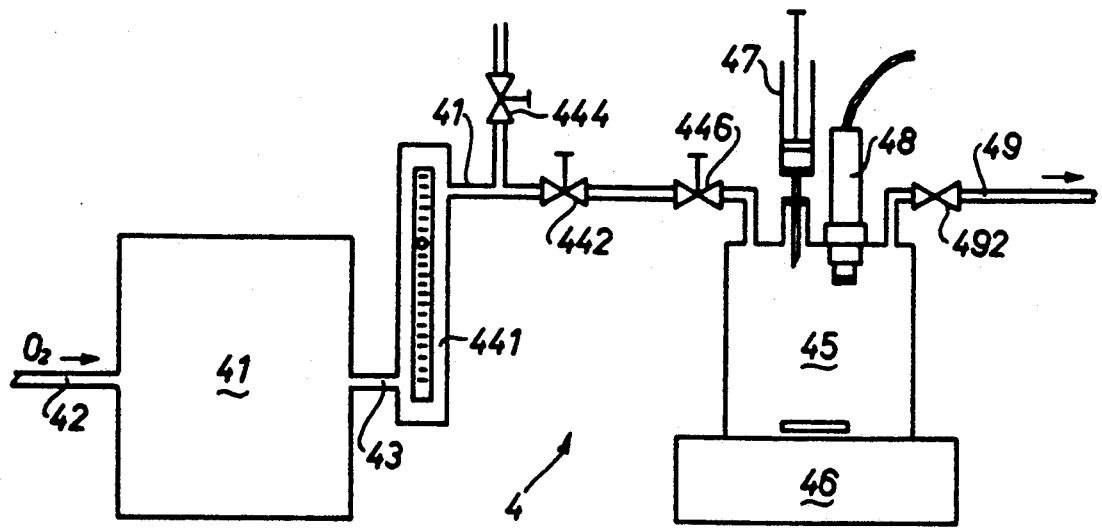
FIG. 4 is a diagram showing the means for absolute calibration of a membrane-enclosed cell.

With reference to FIG. 1, cell 1 includes a sensing electrode 10 having an electroanalytical surface 100 laterally defined by an insulator 11. In amperometry by electroreduction of an electroactive species of interest or EASI the sensing electrode 10 is the cathode; in amperometry by electrooxidation the sensing electrode 10 is the anode. Preferably, the sensing electrode 10 is made of a metal that is chemically inert and a noble metal, gold and gold alloys are preferred for many purposes.

The counter electrode 12 surrounds the insulator 11 and an electrically insulating jacket 17 is provided at the outside of cell 1. Membrane 18 is held on top of cell 1 by means of a holding ring 19.

An aqueous electrolyte 15 containing a redox catalyst RED/OX according to the invention as a solute and in substantially homogeneous distribution is in contact with the surfaces 100, 120 of sensing electrode 10, counter electrode 12 and with the "inner" surface 180 of membrane 18. A predetermined potential between sensing electrode 10 and counter electrode 12 is applied via conduits 101, 121 and the same conduits serve to convey an indicative current signal. Temperature sensing means (not shown) may be provided in a manner known per se. An external sample fluid SF is in contact with the external surface 181 of membrane 18. A reactive agent RA, e.g. a strongly reducing or strongly oxidizing substance, such as ozone, contained in the sample fluid SF permeates membrane 18 because of normal diffusion phenomena. Upon physical contact of the RA with the RED/OX in electrolyte 15, the RA will be transformed, by chemical reaction with the RED/OX, into a transfer species.

In the case of ozone ($O_3$) as RA in the presence of oxygen ($O_2$) the RED/OX enters directly into the ozone detection process as follows:

$$O_3 + \gamma_1 \text{ RED} \longrightarrow O_2 + \gamma_2 \text{ OX in solution}$$

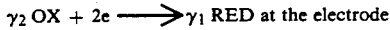
$$\gamma_2 \text{ OX} + 2e \longrightarrow \gamma_1 \text{ RED at the electrode}$$

$\gamma_1$ and $\gamma_2$ are stoichiometric coefficients.

For satisfactory operation in ozone detection RED/OX should have the following properties:

Its redox potential should be as far cathodic as possible (at the pH existing in the sensor) compared to the $O_3O_2$ potential. This is required for fast reaction between the $O_3$ and the RED state of the RED/OX.
In acid solution $E_{O3/O2}=2.07$ V;
in basic solution $E_{O3/O2}=1.24$ V.
With a conventional chloride as RED and one of its oxidation states, e.g. the hypochlorite ion as OX, the $E_O$ of $-0.89$ V of the $Cl^-/ClO^-$ transformation would be too close to the $O_3$ potential, and no significant oxidation would occur.

For ozone detection, the redox potential of RED/OX should, preferably, not be so far cathodic that RED can be rapidly oxidized by $O_2$.
The values are $E_{O2/H2O}=1.23$ V in acid and $E_{O2/OH^-}=0.401$ V in base.

For ozone detection with a cell 1 according to the invention a suitable RED/OX catalyst should generally have a potential that is more anodic than about 0.75 V. On the other hand, RED/OX catalysts with more cathodic potentials might react very slowly with $O_2$, e.g. because of kinetic limitations, yet react quickly with $O_3$.

The OX form of the RED/OX catalyst should not react with water or hydroxide ions, or react but with an insignificant speed. In other words, the presence of the RED/OX catalyst should not significantly catalyze the oxidation of water by ozone.

Preferably, the chemistry of the RED/OX catalyst should be as simple as possible to avoid complications if a number of oxidized species could be formed from RED since not all of these might be reducible at the sensing electrode 10.

Since the counter electrode 12 of cell 1 contacts the electrolyte 15 the RED/OX can react directly at the anode surface 120:

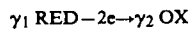
$$\gamma_1 \text{ RED} - 2e \rightarrow \gamma_2 \text{ OX}$$

This reaction should be compatible with general operating conditions of cell 1, of course.

Finally, when measuring ozone as RA, the reduction of the latter tends to raise the pH of the aqueous electrolyte, e.g.

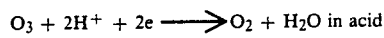
$$O_3 + 2H^+ + 2e \longrightarrow O_2 + H_2O \text{ in acid}$$

or

$$O_3 + H_2O + 2e \longrightarrow O_2 + 2OH^- \text{ in alkali.}$$

Hence, RED/OX must not suffer hydrolysis nor be incompatible in any way with electrolyte 15, e.g. when the latter is alkaline.

With a bromide salt as a preferred RED/OX in electrolyte 15 for measurement of ozone as RA in gaseous phase or dissolved in a normally liquid substance, such as typically water or aqueous media and, practically unavoidable, in the presence of elemental oxygen $O_2$, the following potentials are found (at room temperature) in an alkaline electrolyte 15:

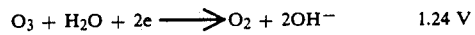
$$O_3 + H_2O + 2e \longrightarrow O_2 + 2OH^- \quad 1.24 \text{ V}$$

$$O_2 + 2H_2O + 4e \longrightarrow 4OH^- \quad 0.401 \text{ V}$$

$$Br^- + 6OH^- \longrightarrow BrO_3^- + 3H_2O + 6e \quad 0.61 \text{ V}$$

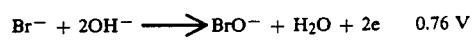
$$Br^- + 2OH^- \longrightarrow BrO^- + H_2O + 2e \quad 0.76 \text{ V}$$

$$2Br^- \longrightarrow Br_2 \text{ (aq)} + 2e \quad 1.087 \text{ V}$$

$$O_3 + \tfrac{1}{3}Br^- \longrightarrow O_2 + \tfrac{1}{3}BrO_3^-$$

Hence, although $Br^-$ is oxidizable by $O_3$, it is stable with respect to $O_2$.

Preferably, with a bromide salt as RED/OX in an electrolyte, the OX state should be the bromate ion $BrO_3^-$ which does not react with water to any significant extent.

It is also required that the presence of the redox catalyst in the electrochemical cell should not interfere in any way with the intended reaction at the counter electrode. For detection of ozone this reaction is conveniently chosen to be the dissolution of a "consumable" or "reactive" metal anode. Silver or a silver alloy is particularly preferred as an anode metal and in this case the use of a high concentration of a bromide salt as redox catalyst is particularly convenient since the resulting precipitate of silver bromide adheres to the silver and hence removes potentially interfering silver ions from the electrolyte

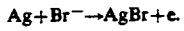

Such a counter electrode 12 is stable Preferred bromide salts are those that are stable in alkaline solution, e.g. those of the alkali metals Na and K. KBr is a preferred catalyst. Generally, it has been found that the reaction of $O_3 + Br^-$ in cell 1 is rapid and that the reduction of $BrO_3^-$ to $Br^-$ in cell 1 is also satisfactory.

The MEAC 2 shown in FIG. 2 includes all elements of cell 1 of FIG. 1 and same elements are indicated by the same second digits in the reference numerals, e.g. the sensing electrode 10 of cell 1 is the sensing electrode 20 of cell 2, the counter electrode 12 corresponds with electrode 22, membrane 18 with 28 and, of course, electrolyte 15 with electrolyte 25 and, again, the external sample SF contains a reactive agent RA which reacts chemically with the catalyst RED/OX provided in electrolyte 25 of a cell 2 according to the invention.

The additional element of cell 2 is a guard electrode 24, an additional insulator layer 23 (since insulator 21 is now between sensing electrode 20 and guard electrode 24) between the guard 24 and counter electrode 22 and an additional lead 241 for maintaining the guard electrode at a predetermined potential, e.g. substantially the potential at the sensing electrode. The guard 24—actually its electrolyte-exposed surface 240—is intended to preclude that electroactive species arrive at surface 200 of sensing electrode 20 except directly from the layer of electrolyte between surface 200 and the geometrically corresponding portion of the inner surface 280 of membrane 28.

It is to be noted that MEACs having the general structure shown in FIGS. 1 and 2 are obtainable commercially, e.g. for oxygen sensing, from ORBISPHERE LABORATORIES (Geneva, Switzerland) and that such MEACs can be converted into ozone detecing MEACs according to the invention. Details of preferred structural features of and peripheral devices for the commercially available sensors can be found in the patent literature, e.g. in U.S. Pat. Nos. 4,096,047, 4,153,149, 4,563,249, 4,585,542, German Patents Nos. 2,851,447, 4,339,634, European Patents Nos. 0 043 611 and 0 085 450. Further, the electrical guard of the MEAC of FIG. 2 might be modified as shown in European Patent No. 0 205 399. Accordingly, these features shall not be discussed herein.

For example, conversion of a commercially available oxygen sensor of the type mentioned above into a MEAC for quantitative ozone measurement will normally require but an exchange of the catalyst and of the membrane when relative calibration is to be used at the measuring site. Since calibration of ozone detection devices is a particular and hitherto incompletely resolved problem, this aspect will now be explained in some detail.

First, a method of "absolute calibration" will be explained with reference to FIG. 4. Apparatus 4 shown therein includes a conventional ozone generator or ozonator 41 supplied via conduit 42 with a stream of oxygen or air. The ozone-containing gas stream is fed via conduit 43 through a flow meter 441, and a number of valves, e.g. 444 and 442 or 446 are provided in conduit 44 which then opens into a titration vessel 45. The latter includes a magnetic stirring equipment 46, a syringe 47 for introduction of a chemical titration agent, and an ozone detecting MEAC 48. A feed line 49 is provided with a valve 492 for venting the titration vessel.

The ozonator 41 converts a fraction of the oxygen supplied via conduit 42 into ozone. The magnitude of the fraction depends upon the flow rate of gas as well as the settings of controls on the ozonator; hence, the flow meter 441 is a necessary element of apparatus 4. Although the fraction can remain constant over the short term, it tends to vary by as much as ±20% over the long term.

Needle valves 442 and 444 enable some of the $O_3/O_2$ mixture to be flushed through the titration vessel. By closing first valve 446 then valve 492, a fixed volume of this mixture, at a known pressure, can be isolated in vessel 45.

Assuming that the volume V of vessel 45 is filled with an $O_3/O_2$ gas mixture at total pressure $P_t$ and that the partial pressures and mole fractions of the component gases are $P_{O3}$, $x_{O3}$, $P_{O2}$, $x_{O2}$ $$P_{O3} = x_{O3} \cdot P_t \text{ and } P_{O2} = x_{O2} \cdot P_t.$$

The ozone sensor or MEAC 48 exposed to the mixture produces a current $$I_O = k P_{O3}$$

wherein k is the sensitivity (μA/bar) of MEAC 48.

Assuming that a volume v of a solution of sodium arsenite (or another known reducing agent) at a concentration C molar equivalents per unit volume is added to the gas volume, and since the number of equivalents of arsenite is $C \cdot v$, the same number of moles of $O_3$ is removed, the number of moles of $O_3$ remaining is $$\eta_{O3} - C \cdot v \text{ (assuming that } \eta_{O3} > C \cdot v).$$

This ozone is now distributed between the gas and liquid phases. What is needed is to know how the gas is distributed in order to calculate the partial pressure of ozone in the gas phase.

Assuming equilibrium between gas and liquid (after completion of the reaction) and a negligible rate of decomposition of the ozone in the liquid, the dissolved concentration of $O_3$, $C_{O3}$, is related to the new partial pressure of $O_3$ in the gas by:

$$C_{O3} = S_{O3} \cdot P_{O3}$$

wherein $S_{O3}$ is the solubility of ozone in the liquid. So:

$$\eta_{O3} - C \cdot v = \underbrace{C_{O3} \cdot v}_{\text{moles in liquid}} + \underbrace{(V - v) \cdot P_{O3}/RT}_{\text{moles in gas}} =$$

total moles of ozone $$P_{O3} \cdot [(V - v)/RT + v \cdot S_{O3}]$$

that is:

$$P_{O_3} = \frac{\eta_{O_3} - C \cdot v}{\frac{(V-v)}{RT} + v \cdot S_{O_3}}$$

The new current I from the ozone sensor is:

$$I = \frac{k \cdot \frac{RT}{V}(\eta_{O_3} - C \cdot v)}{1 - \frac{v}{V}(1 - S_{O_3} RT)}$$

This is the equation for the relationship between the sensor current and the volume of reducing agent added. The unknowns are k, the sensitivity of the sensor, and $\eta_{O_3}$ the original number of moles of ozone in the volume V.

According to the foregoing equation it should be possible to construct a straight-line plot of the form shown in FIG. 2A of the drawings.

In practice, one finds that experimental data at low volumes of added reducing agent fit this model but data near the end point of the titration are distorted due to continuous decomposition of ozone in the aqueous phase. It is preferred, therefore, to make an addition $v_1$ of reducing agent which is well below the final volume $v_f = \eta_{O_3}/C$ equivalent to the original ozone.

Let the current after this addition be $I_1$; then the formula $$\eta_{O_3} = \frac{C \cdot v_1}{1 - \frac{I_1}{I_0}\left[1 - \frac{v_1}{V}(1 - S_{O_3} RT)\right]}$$

gives a good estimate of the original number of moles of ozone in the volume V.

The mole fraction $x_{O_3}$ of ozone in the original mixture is:

$$x_{O_3} = \eta_{O_3}/N_t$$

wherein $N_t$ is the total number of moles of gas (including oxygen and any other components of the mixture) in the volume.

$N_t$ can be calculated assuming the mixture to be an ideal gas:

$$N_t = P_t V/RT.$$

Hence, $x_{O_3}$, and $P_{O_3} = x_{O_3} \cdot P_t$ can be calculated. The percentage by volume of ozone in the original mixture is $100 \cdot x_{O_3}$.

Finally, the sensitivity of the ozone sensor can also be calculated:

$$k = I_0/P_{O_3}$$

permitting calibration of MEAC 48. A specific example will be given below.

Absolute calibration of a MEAC for quantitative ozone determination according to the invention could be done with liquid samples, i.e. ozone dissolved in water. In view of the tendency of ozone to react with water, it is an advantage of the invention that absolute calibration with gaseous samples is feasible. Since there is a known relationship between the compositions of gaseous and aqueous media which would generate the same current in an ozone sensing MEAC according to the invention, the signal obtained can be calibrated to an aqueous concentration even though the MEAC is calibrated in a gaseous sample.

According to Henry's law, the concentration C of ozone in water which would produce the same sensor current as a gas at a pressure P containing a percentage x of ozone would be given by:

$$C = 10^4 \cdot \frac{M_{O_3}}{M_{H_2O}} \cdot \frac{xP}{K_H} \text{ ppm}$$

wherein $M_{O_3}$ and $M_{H_2O}$ are the molecular weights of ozone and water, respectively, and $K_H$ is the usual Henry's law constant. Concentration values can be calculated from this formula for a gas containing 1% by volume ozone (x=1), for various total pressures P (mbar) and temperatures t (°C.). In the calculation of these tabulated values of C, a formula for $K_H$ can be taken from Roth, J. A. and Sullivan, D. L., IUPAC Solubility Data Series, Vol. 7 (oxygen and ozone), page 474, Pergammon Press, Oxford 1981.

According to an important aspect of the invention, a MEAC for quantitative ozone determination can be calibrated by a "relative" method, i.e. in the absence of ozone and on the basis of a predetermined ratio of the permeation rate of ozone through a given membrane material, on the one hand, and the permeation rate of oxygen through the same membrane material, on the other hand.

Since the normal oxygen concentration of air is universally constant, simple calibration in air is possible according to the invention in on-site ozone detection on the basis of absolute measurements made under fully reproducible laboratory conditions.

Figure 5:
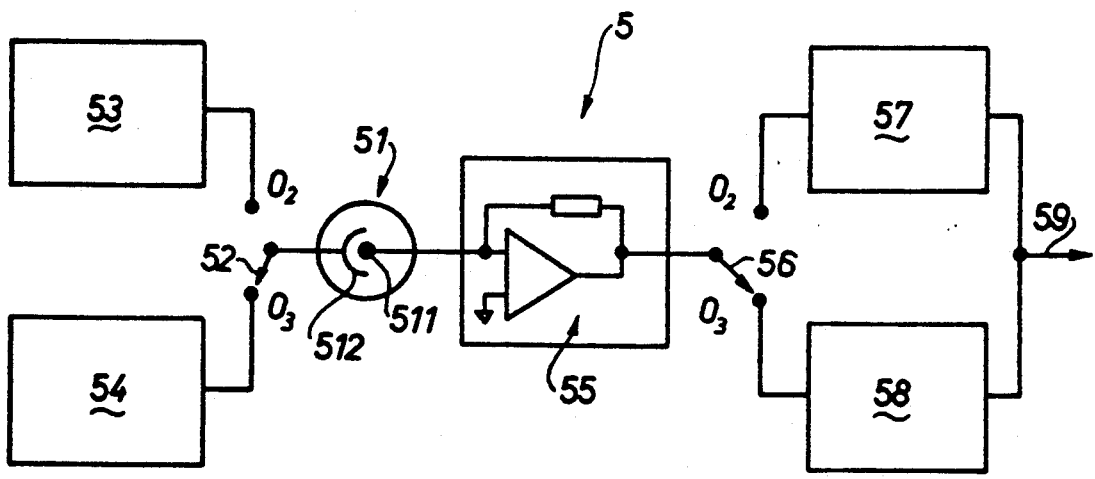
FIG. 5 is a diagram showing the means for relative calibration of an ozone sensor according to the invention.

FIG. 5 shows a diagram of an apparatus 5 embodying this aspect. It includes a MEAC 51 according to the invention as explained in connection with FIG. 1 having a sensing electrode (cathode 511) and a counter electrode (anode 512).

A first switch means 52 is provided to alternatively connect anode 512 with a first source 53 for a predetermined voltage for oxygen detection or a second source 54 for a predetermined voltage for ozone detection.

Cathode 511 of MEAC 51, on the other hand, is connected with a current-to-voltage converter 55 having its output connected with a second switch means 56 for alternatively connecting the signal current either with a compensation amplifier 57 for oxygen (e.g. for temperature compensation) or with a compensation amplifier 58 for ozone. Both amplifiers 57, 58 are connected with a display or recorder for the final output signal.

Typically, a voltage of −0.25 V applied to anode 512 will cause MEAC 51 to detect ozone alone while raising the anode voltage to +0.7 V enables the reaction of either or both of oxygen and ozone at the cathode. Switch 52 selects the appropriate voltage, instrument gain and temperature coefficient for the correct display at 59 of the concentrations of the two gases in whatever units are chosen.

The converter 55 holds cathode 511 of MEAC 51 at ground potential, hence maintaining the cell voltage constant no matter what current flows. It also converts the current into a proportional voltage.

The amplifiers 57, 58 may perform merely a temperature compensation or/and a correlation of the sensor current. This is necessary because the rate of permeation of the gases through the sensor membrane varies with temperature and because a correlation with permeation rates may be needed if "indirect" or "air calibration" is used.

Generally, the amplifiers 57, 58 may perform other temperature dependent tasks such as the conversion of the directly measurable "fugacity" of the gas (that is, the number of collisions of gas molecules with unit area of the membrane, per unit time) into units of concentration such as milligrams of gas per kilogram of solution. These temperature effects differ for oxygen and for ozone, hence the current has to be routed through different circuit elements when calibrating in air and when measuring ozone. This rerouting is handled by one pole of the second switch 56 in FIG. 5. One convenient way of performing temperature compensation is to include thermistors as negative feedback of the second amplifier 58. Such techniques are well known to persons skilled in the art.

Other configurations of the circuit shown in FIG. 5 are possible. For example, it is feasible to combine the temperature compensation function with the current to voltage conversion.

The "relative" method according to the invention for calibration of a MEAC on-site, preferably with the oxygen content of ambient air as the calibrating standard, is based on the fact that the ratio of the permeation rates $P_x$, $P_y$ of any two different gases x, y through the same membrane is roughly constant:

$$\frac{P_x}{P_y} = k$$

Thus, k is a characteristic of the membrane material. In particular, then the number of molecules of oxygen which permeate per second, per unit partial pressure difference and per square centimeter through any given membrane should bear a substantially constant ratio to the number of ozone molecules permeating under the same conditions:

$$P_{O2}/P_{O3} = k$$

The permeation rates of oxygen and ozone were measured through twenty different membranes made from perfluoroalkoxy Teflon (Du Pont de Nemours) all nominally 25.4 μm. Oxygen permeation rates varied from $$P_{O2} = 0.95 - 1.2 \cdot 10^{-9} \text{ mol } (cm^2 \cdot sec \cdot bar)^{-1}$$

and ozone permeation rates from $$P_{O3} = 1.55 - 1.9 \cdot 10^{-9} \text{ mol } (cm^2 \cdot sec \cdot bar)^{-1}$$

The ratio varied in the range:

$$P_{O2}/P_{O3} = 0.63 \pm 0.03 \text{ at } 25° \text{ C.}$$

Individual permeation rates vary by ±10%, yet their ratio varies by only ±5%. The individual permeation rates and their ratio vary with temperature.

This fact is exploited for "relative" calibration according to the invention. In essence, this requires determination of the permeation rate of ozone through the sensor membrane. From the foregoing it follows that one can instead determine the permeation rate of oxygen, then apply the factor $P_{O2}/P_{O3}$ to calculate what would be the permeation rate of ozone with an uncertainty of only about ±5%.

Determination of the permeation rate of oxygen through the sensor membrane is, of course, much simpler than that of ozone because the air provides a source of a known oxygen partial pressure. On the other hand, determination of the ozone partial pressure in the gas issuing from an ozonator is not a simple task for use in on-site ozone detection.

For practicing such relative or "air calibration" of an ozone sensor the switches 52 and 56 are each marked in the appropriate switching positions as "Air Calibration" and "Ozone Measurement". For "Air Calibration", the −0.7 V voltage is applied to anode 512 and the output from the converter 55 is compensated in a manner known per se, e.g. by digital or analogue means, for the effects of temperature upon the oxygen permeability of the membrane, and the gain of the amplifier 57 is adjusted to produce a correct signal for the oxygen content of the external sample, preferably air.

This may involve adjustment of a potentiometer (not shown in FIG. 5) to cause fine tuning of the gain. Upon exposure to air for "relative" calibration a preset setting can be used.

Upon switching to the "Ozone Measurement" position, a voltage of +0.25 Volts is applied to the cathode 511 with respect to the Ag/AgBr anode 512; then, the sensor current is appropriately compensated for the effects of temperature upon the ozone permeability of the membrane and for correlation with a factor derived from the previously determined permeation rates of the membrane material in question for oxygen and ozone.

In this manner, the ozone content of the sample can be displayed at output 59 with a potential error of generally below ±5%.

FIGS. 3A and 3B are shown to illustrate the current function in absolute calibration (FIG. 3A) by chemical titration using the MEAC according to the invention as an end point indication in line with the calculations explained above.

FIG. 3B, on the other hand, is to explain that a MEAC according to the invention will be selective for ozone in the presence of elemental oxygen by selecting an appropriate cell voltage. With a voltage of typically in the range of from +400 mV to +50 mV (sensing electrode is positive) with respect to an Ag/AgBr electrode, on the other hand, a current rise due to the reduction of $O_2$ is noticeable at potentials more negative (cathodic) than 50 mV. Hence, the area or plateau $D^1$ left of the Zero potential line represents the diffusion-limited reduction of ozone at a chosen potential of, say, +250 mV while the plateau at the right side represents the diffusion-limited reduction of ozone plus oxygen. The ordinate i represents the current which, in actual practice, would be much higher with regard to the oxygen current than the ozone current since the latter will normally be accompanied by an excess of oxygen.

Generally, for determining strongly oxidizing chemical agents with a MEAC including a redox catalyst dissolved in the electrolyte, the electrolyte will be alkaline (above pH =7) with a first indirect calibrating voltage between Zero and −1.5 V and a second or measuring voltage between Zero and +1.5 V.

For determining strongly reducing chemical agents according to the invention the electrolyte will, in general, be acid (less than pH=7) with a first or indirect calibrating voltage between Zero V and +1.5 V and a second or measuring voltage between −1.5 V and Zero V.

Specific examples illustrating the invention are given below.

EXAMPLE 1

The apparatus used was essentially as shown in FIG. 4. The MEAC 48 was a sensor, Model 28031, by OR-BISPHERE LABORATORIES, Geneva, Switzerland, with a sensing electrode of gold (area 0.3142 cm$^2$) and an anode of silver supplied with an aqueous electrolyte composed of 0.6 gram per liter of KOH and 120 gram per liter of KBr. The membrane had a thickness of 25.4 $\mu$m and consisted of commercial perfluoroalkoxy teflon, e.g. TEFLON PFA (trademark by Du Pont).

An ozone containing gas mixture was enclosed in the titration vessel 45 having a 197 ml volume at 25° C. and at 0.972 bars pressure. The initial indication on the ozone analyzer with the sensor exposed to this mixture was 2.47 $\mu$A. An addition of 2.354 ml of 0.1 molar ferrous sulphate solution in water was made and the analyzer indication changed to 0.922 $\mu$A.

Application of the foregoing formulae results in the following values:

$\eta_{O_3} = 1.868 \cdot 10^{-4}$ moles $O_3$ $N_t = 7.725 \cdot 10^{-3}$ moles of gas $x_{O_3} = 0.0242$ $P_{O_3} = 0.0235$ bars $k = 105.1$ $\mu$A/bar $\geq 1.73 \cdot 10^{-9}$ mol(cm$^2$·s·bar)$^{-1}$ Hence, the original gas mixture is revealed to have contained 2.42% by volume of ozone using this titration method in which the MEAC 48 is used as an end point indicator.

The gas mixture was produced by a commercial ozonator, type BL1 (Blatter AG, Basel, Switzerland), operated at 180 V with 50 liter/hour pure $O_2$.

EXAMPLE 2

The apparatus used was essentially as shown in FIG. 5.

The permeation factor k was determined from the ozone permeation rate as obtained in Example 1; the oxygen permeation rate was $1.06 \cdot 10^{-9}$ mol/(cm$^2$·s·bar), giving a ratio $P_{O_2}/P_{O_3} = 0.61$.

Then, the MEAC was first calibrated in air and subsequently exposed to an ozone/oxygen mixture as used in Example 1. The results were as follows:

| | |
|---|---|
| Temperature: | 25° C. |
| Barometric pressure: | 970 mbar |
| Indicated partial pressure of ozone: | 23.2 mbar |
| Fraction of ozone in gas mixture: | $\frac{23.2}{970} \cdot 100 = 2.39\%$ |

This same gas mixture was titrated with ferrous sulphate, as already described in Example 1, reading sensor current instead of the indicated partial pressure of ozone. Hence, the results of the two independent methods of calibration, namely 2.42% by volume by titration and 2.39% by volume by air calibration compare favorably.

Repetition of this operation yielded a reproducibility of ±5%.

EXAMPLE 3

An apparatus substantially as shown in FIG. 4 was used to calibrate a MEAC 48 for measuring ozone according to the invention. The titration vessel 45 was a flask having a volume of 186.2 ml immersed in a constant temperature bath at 25° C.

A gas stream containing ozone produced in a standard ozonator (Type BL1, Blatter AG, Basel, Switzerland) was flushed through the flask until the MEAC 48 gave a constant signal of 2.95 $\mu$A; then, two milliliters of (0.05 mol/liter sodium arsenite) reducing agent was added and vigorously stirred with the magnetic stirring bar. The output from the amperometric sensor diminished to 1.448 $\mu$A in 3 minutes. Assuming complete oxidation of arsenic(III) to As(V) by the ozone:

$$NaAsO_2 + O_3 + H_2O \rightarrow NaH_2AsO_4 + O_2$$

the number of moles of ozone removed is:

$$0.002 \times 0.05 = 0.0001 \text{ moles}.$$

This number of moles of ozone was responsible for the incremental current:

$$2.95 - 1.448 = 1.502 \ \mu A.$$

Hence, the original current of 2.95 $\mu$A was generated by $$\frac{2.95}{1.502} \times 10^{-4} = 1.964 \times 10^{-4} \text{ moles of ozone}$$

The results of this titration were plotted as shown in FIG. 3C to represent a calibration curve for MEAC 48.

Various modifications of the devices and examples will be apparent to one skilled in the art. For example, membranes made of other polymers, e.g. FEP TEFLON (polymer of fluorinated ethylene/propylene), TEFZEL (copolymer of ethylene and tetrafluoro ethylene) or other polymer membranes known to be suitable for oxygen detection could be used provided they are substantially inert to ozone at the ozone concentration of interest.

Generally, all components except the redox catalyst should not undergo any significant change upon use under the operatin conditions of the MEAC for determining the strongly oxidizing or strongly reducing chemical agents in accordance with the present invention.

Finally, the novel indirect calibration method disclosed herein for use in ozone detection can be applied to calibration of other systems for detecting and monitoring strongly reactive substances from the oxidizing group (i.e. exhibiting a potential, as measured above for ozone, of at least about +1.3 Volts) which includes other water-reactive oxidizing substances as, typically, chlorine ($Cl_2$), fluorine ($F_2$) and sulphur trioxide ($SO_3$) and strongly reducing substances including such agents as hydrogen sulphide ($H_2S$), sulphur dioxide ($SO_2$), nitrous oxide ($N_2O$), carbon monoxide (CO) and other substances showing a potential (measured as indicated above for ozone) that is more cathodic (i.e. more negative) than zero Volt.

The advantages of the present invention as well as certain changes and modifications of the disclosed embodiments thereof will be readily apparent to those skilled in the art. It is the Applicant's intention to cover by his claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that prior art allows.

What is claimed is:

1. A method of calibrating an instrument for use in measuring a concentration of a strongly reactive chemical agent; said method comprising the steps of:
   (a) providing an enclosed space containing a first amount of a strongly reactive chemical agent in a fluid;
   (b) introducing into said enclosed space a metered quantity of a chemical reactant capable of quantitatively reacting with said strongly reactive chemical agent for eliminating a second amount of said first amount of said strongly reactive chemical agent from said enclosed space in proportion with said introduction of said chemical reactant;
   (c) monitoring said fluid by means of an amperometric cell for determining the concentration of a strongly reactive chemical agent in a fluid external to said cell; said cell comprising a sensing electrode and a counter electrode each having a surface exposed to an aqueous electrolyte which is separated from said fluid by a membrane that is permeable to said strongly reactive chemical agent in said fluid but is substantially impermeable to said aqueous electrolyte;
   and said aqueous electrolyte comprising a redox catalyst for chemically transforming said strongly reactive chemical agent within said cell into an intermediary electroactive species capable of generating an indicative electrical signal in proportion with said concentration of said strongly reactive chemical agent; and
   (d) determining by said amperometric cell an end point concentration indicative of titrimetric neutralization of said strongly reactive chemical agent by said chemical reactant.

2. The method of claim 1 wherein the strongly reactive chemical agent is ozone.

3. The method of claim 1, wherein said redox catalyst is taken from the group consisting of $Tl_2SO_4$, $FeSO_4$, $Na_3(IrCl_6)$, $Na(AsO_2)$, KBr, NaBr, LiBr, and KI.

4. The method of claim 1 wherein said redox catalyst has a concentration in the range of approximately 0.05 to 5 moles per liter.

5. The method of claim 1, wherein said redox catalyst is KBr.

6. The method of claim 1, wherein said chemical reactant is taken from the group consisting of sodium arsenite and ferrous sulfate.

7. The method of claim 1, wherein said chemical reactant is sodium arsenite.

8. The method of claim 1, wherein said strongly reactive chemical agent is in the gaseous phase.

9. The method of claim 3, wherein said redox catalyst has a concentration in the range of approximately 0.05 to 5 moles per liter.

10. The method of claim 1, wherein said strongly reactive chemical agent is ozone, wherein said chemical reactant is sodium arsenite and wherein said redox catalyst is potassium bromide.

11. The method of claim 10, wherein said redox catalyst has a concentration in the range of approximately 0.05 to 5 moles per liter.

* * * * *